(12) United States Patent
Castillo et al.

(10) Patent No.: US 8,986,979 B2
(45) Date of Patent: Mar. 24, 2015

(54) CELL CULTURE DEVICE AND METHOD OF CULTURING CELLS

(75) Inventors: José Castillo, Brussels (BE); Jean-Christophe Drugmand, Louvain-la-Neuve (BE)

(73) Assignee: Pall Artelis BVBA, Brussels (BE)

( * ) Notice: Subject to any disclaimer, the term of this patent is extended or adjusted under 35 U.S.C. 154(b) by 679 days.

(21) Appl. No.: 13/129,163

(22) PCT Filed: Nov. 13, 2009

(86) PCT No.: PCT/EP2009/065170
§ 371 (c)(1),
(2), (4) Date: May 13, 2011

(87) PCT Pub. No.: WO2010/055143
PCT Pub. Date: May 20, 2010

(65) Prior Publication Data
US 2011/0223582 A1    Sep. 15, 2011

(30) Foreign Application Priority Data
Nov. 13, 2008   (GB) .................................. 0820779.7

(51) Int. Cl.
C12M 1/34        (2006.01)
C12M 3/00        (2006.01)
C12M 1/00        (2006.01)

(52) U.S. Cl.
CPC ............... *C12M 41/36* (2013.01); *C12M 23/26* (2013.01); *C12M 23/28* (2013.01); *C12M 23/34* (2013.01)
USPC .................. 435/287.1; 435/286.1; 435/289.1; 435/3; 435/29

(58) Field of Classification Search
CPC ...... C12M 23/26; C12M 23/28; C12M 23/34; C12M 41/36
USPC ....................... 435/3, 29, 286.1, 287.1, 289.1
See application file for complete search history.

(56) References Cited

U.S. PATENT DOCUMENTS 5,501,971 A    3/1996  Freedman et al.
2003/0070942 A1  4/2003  Ossart
(Continued)

FOREIGN PATENT DOCUMENTS

DE    102006001623 A1    7/2007
FR       2812725 A1    2/2002
(Continued)

OTHER PUBLICATIONS

Database WPI, XP-002575823, Cell Cultivation Bag, Jan. 1, 1991, Week 199109, Thompson Scientific, London, GB.
(Continued)

*Primary Examiner* — Michael Hobbs
(74) *Attorney, Agent, or Firm* — King & Schickli, PLLC

(57) ABSTRACT

The present invention relates to a cell culture device (1) comprising a disposable culture vessel comprising at least one external wall made of a material having a Young modulus E of less than 50 GPa, in which there is situated at least one cell culture zone and at least one cell-free medium transfer zone, allowing a flow of a culture medium between the cell culture zone and the transfer zone, and at least one sensor element of a cell-density sensor wherein said sensor element is situated in the cell culture zone of said vessel. The sensor element is an electrode arrangement of at least two and preferably at least four measuring electrodes arranged on the inner side of an external wall of the disposable culture vessel and directed towards the cell culture zone. The present invention further relates to a method of culturing cells.

34 Claims, 10 Drawing Sheets

(56) References Cited

U.S. PATENT DOCUMENTS

| | | |
|---|---|---|
| 2005/0112544 A1 | 5/2005 | Xu et al. |
| 2005/0272146 A1 | 12/2005 | Hodge et al. |
| 2007/0159920 A1 | 7/2007 | Baumfalk et al. |
| 2008/0032389 A1 | 2/2008 | Selker et al. |
| 2008/0206847 A1* | 8/2008 | Kunas et al. ............ 435/287.1 |
| 2009/0104594 A1* | 4/2009 | Webb .............................. 435/3 |

FOREIGN PATENT DOCUMENTS

| | | |
|---|---|---|
| GB | 2177801 A | 1/1987 |
| JP | 03010677 | 1/1991 |
| JP | 03010677 A1 | 1/1991 |
| WO | 2007039600 A1 | 4/2007 |
| WO | WO 2007/039600 | 4/2007 |
| WO | 2007134267 A2 | 11/2007 |
| WO | WO 2007/134267 | 11/2007 |
| WO | WO 2008/005998 | 1/2008 |
| WO | 2010010313 A2 | 1/2010 |

OTHER PUBLICATIONS

Internet Archive WayBackMachine Wavebiotech http://www.wavebiotech.net/site_v2/biowave2_e.asp 1 Page.
Wave Biotech BioWave 2SPS broushure 2 Pages.
Elastizitatsmodul http://de.wikipedia.org/wiki/Elastizit%C3%A4tsmodul Printed: Jan. 13, 2015 (English translation: http://en.wikipedia.org/wiki/Young%27s_modulus).

* cited by examiner

CELL CULTURE DEVICE AND METHOD OF CULTURING CELLS

This application is the national stage of PCT/EP2009/065170, filed Nov. 13, 2009, which claims priority from British Patent Application Ser. No. 0820779.7, filed Nov. 13, 2008, the disclosures of which are incorporated herein by reference.

FIELD OF THE INVENTION

The present invention relates to a cell culture device and a method of culturing of cells and other micro-organisms.

TECHNICAL BACKGROUND

A cell culture device is known from WO 2007/039600 A1, which describes a culture vessel of a bioreactor in which there is situated a culture zone external to an internal medium transfer channel. The cells are situated in the culture zone, which is a sort of basket comprising carriers. This device further comprises culture medium circulation means, allowing a circulation of the culture medium through the culture zone and the transfer zone, and an optical sensor element for measuring a culture parameter of the cell culture. This device can be disposable thus eliminating complications caused by sterilization.

Another type of culture device is known from EP 1 333 085 A2 which describes a culture vessel of small size, with a first chamber containing a cell culture zone with substrate means for cell attachment, and a second chamber connected to the first chamber to facilitate the culture medium to flow freely between the first and the second chamber through the cell culture zone. This device can be disposable thus eliminating complications caused by sterilization and is capable of intermittently provide oxygen and nutrients to cells by controlling the amount of culture medium that comes into contact with the growth substrate means in the cell culture zone.

Ducommun et al. (Biotechnology and bioengineering, Vol. 77, No 3, Feb. 5, 2002) describes the use of a biomass (cell density) probe into a fixed bed bioreactors. The probe Biomass Monitor® 214M used is commercially available and is a pencil-shaped-type probe incorporating four electrodes. The use of this type of probe is typically performed by fitting the pencil-shaped probe in an aperture of the lid of a rigid culture vessel (here made of stainless steel and/or glass). This type of culture vessel, whether made of glass or stainless steel, have as a main characteristic, the rigidity of their walls and the consistency of all their dimensions. This is of high importance for the implementation of biomass probes based on capacitance. Such a probe works by applying a low current RF field to the biomass immobilised within 20 to 25 mm of the four electrodes of the sensor. In this system according to the prior art, the rigidity of the walls permit to avoid that the position of the probe could be modified and thereby the packing of the fixed bed be modified. Such rigid culture vessels makes the device comprising them expensive. This increases the cost of the device and imposes a recycling of the culture vessel which itself imposes expensive washing and sterilisation steps.

SUMMARY OF THE INVENTION

An object of the present invention is to provide an economical compact device which is suitable even for smaller vessels.

This object is addressed by the subject-matter of the attached claims. Preferred embodiments are described in the sub-claims.

It is an advantage of embodiments of the present invention that inexpensive devices comprising a disposable culture vessel can be obtained while simultaneously assuring accurate sensing within the culture zone of said culture vessel, this even when the walls of the vessel deform e.g. due to gas overpressure or mechanical shock. Essentially for reasons of costs, a less rigid, disposable culture vessel is preferably used for the cell culture device. The known device architectures do not permit the use of a biomass probe in such disposable devices. FIG. 6 illustrates a problematic situation solved by the first and second particular embodiment of the first aspect of the present invention. In the left part of FIG. 6, a pencil-shaped probe 11 comprising four electrodes (not shown) is shown in a fixed bed bioreactor. The circles 43 are a representation of the low current RF field applied by the probe to its surrounding (fixed bed 44). This field typically extends 20 to 25 mm in the fixed bed 44 and defines an active volume. This field enables the measurement of the cell density. At the center of FIG. 6, the same probe is represented after that the position of the probe has been modified, due to a mechanical action on it (due to the low rigidity of the culture vessel walls). Such a relative movement between a probe and a fixed bed is very likely to happen accidentally during manipulation of such a device, if the walls of the vessel are not very rigid. This movement is responsible for a modification (here a compression) of the fixed bed packing 45 and modifies the amount of cells in the active volume of the probe. The right side of FIG. 6 shows a situation wherein the same pencil-shaped probe 11 is brought back to its original position. The compressed fixed bed packing 45 is still present and a void 46 is additionally present, itself having an important impact on the response of the probe by diminishing the amount of cells in the active volume of the probe. FIG. 6 illustrates the non-reversibility of the impact of any relative movement of a pencil-shaped probe relative to a fixed bed. Such a problem is avoided in the prior art by using cell culture devices comprising a culture vessel having all its external walls made of a rigid material having a high Young modulus such as stainless steel or glass. This increases the cost of the device and imposes a reuse requirement on the culture vessel which itself imposes expensive washing and sterilisation steps. The first and second particular embodiments of the first aspect of the present invention are alternative solutions to this problem. The first particular embodiment of the first aspect of the present invention solves this problem by having a sensor element situated in the culture zone, arranged on a wall delimiting the culture zone and directed towards the cell culture zone. The second particular embodiment of the first aspect of the present invention solves this same problem by having at least one sensor element at least partly situated in the cell culture zone of said vessel and not in direct contact with the casing of the culture vessel, wherein the cell culture device further comprises means for absorbing displacements of the at least one external wall so that the displacement of this wall does not result in a displacement of the sensor element. In other words, the cell culture device comprises means for decoupling movements of the walls from movements of the sensor element. These embodiments solve the problem of how to provide a cell culture device comprising a disposable culture vessel having at least one external wall (and preferably all external walls) made of a material having a Young modulus E of less than 50 GPa (preferably from 0.5 to 40 GPa, more preferably form 0.8 to 30 GPa, even more preferably from 1 to 20 GPa, most preferably from 1.5 to 10 GPa or from 1.5 to 4 GPa), while simultaneously ensuring accurate biomass measurement.

It is a further advantage of embodiments of the present invention that the device can be made very compact and nevertheless functionally effective.

In a first aspect, the present invention relates to a cell culture device comprising a culture vessel, preferably a disposable vessel. The vessel can be a single container or can contain several containers building a closed system by providing medium communication with one another. The volume of the vessel preferably ranges from 10 ml to 250 liters. According to embodiments of the present invention, efficient cell culture devices are obtainable having very small dimensions such as 10 ml to 500 ml, 10 ml to 300 ml, 10 ml to 100 ml or 10 ml to 50 ml. The vessel can have any shape, but it is preferably cylindrical. The vessel can have any number of external walls. External walls are walls separating the interior of the vessel from the outside world. For instance, a rectangular parallelepiped vessel will have 6 walls and a cylindrical vessel will have 3 external walls (top external wall, bottom external wall and a wall delimiting the cylinder laterally). In embodiments, the top external wall can be a removable lid. At least one cell culture zone and at least one cell-free medium transfer zone is situated in said vessel, allowing a flow of a culture medium between the cell culture zone and the cell-free medium transfer zone. The cell culture zone is a volume within the culture vessel comprising cells in culture. The cells are contained in the cell culture zone and are at least partially isolated from the rest of the culture vessel by impermeable and semi-permeable walls. In other words, the cell culture zone is at least partially delimited by external and/or internal walls of the disposable culture vessel (which serve as walls for the cell culture zone). As used herein the term "wall" include also membranes. Preferably, two or more of the walls delimiting the cell culture zone are semi-permeable (i.e. permeable to the culture medium but impermeable to the carriers and/or the cells). The cell-free medium transfer zones are zones of the culture vessel which are free of cells, but which are provided to comprise and circulate the culture medium necessary for the cell culture. The culture medium is normally a liquid aqueous solution. The different zones can have any shape and any arrangement, but certain shapes and arrangements are preferred. In general, if the culture vessel is cylindrical, cylindrical shapes for the cell culture zone and the cell-free medium transfer zones are preferred. Within the body of the culture vessel, a top portion of the vessel is preferably used as a cell-free medium transfer zone. This zone will be hereinafter simply referred to as the top zone. In some embodiments (see for instance the first and second particular embodiment of the present invention), a bottom portion of the vessel may be used as a cell-free medium transfer zone. This zone will be hereinafter simply referred to as the bottom zone. Such a bottom zone when present, and in certain embodiments, is particularly useful to comprise driving means for driving the flow of the culture medium within the culture vessel and through the cell culture zone. A bottom zone is not always necessary (see for instance the third particular embodiment of the first aspect of the present invention. When driving means are foreseen within the culture vessel, further zones other than the culture zone, the top zone and the optional bottom zone are preferably present within the culture vessel. These zones can be internal to the cell culture zone (e.g. forming a cylinder around which an annular cell culture zone is arranged) and/or external to the cell culture zone (e.g. forming an annulus around the cylindrical or annular cell culture zone). In embodiments, the ratio between the volume reserved for the cell-free culture medium (or the volume of the cell free medium transfer zone) and the volume of the cell culture zone may be about 0.5:1 to about 10:1 such as e.g. 2:1 to 4:1 or 1.5:1 to 3:1. In embodiments, at least one driving means for driving the flow of the culture medium within the culture vessel and through the cell culture zone may be present as a part of said cell culture device. In embodiments, the driving means may be situated in the disposable culture vessel or may be outside of the disposable culture vessel. Having the driving means inside the culture vessel permits a more compact design for the device to be obtained. Having the driving means outside of the culture vessel (e.g. in the form of a pump) permits the cost of the disposable culture vessel to be reduced. The purpose of circulating the culture medium is to bring oxygen and nutrients homogeneously to all the cells. The driving means is preferably adapted for being activated without any penetration of the a device wall. A drive is preferably provided by a magnetic coupling through a device wall. The driving means preferably comprises an impeller driven by a drive motor, wherein said impeller is situated in the vessel. The driving means can further comprise at least one flow-guide member and/or a culture-medium inlet and outlet. In particular, the drive motor may be a magnetic drive and the impeller may be a magnetic impeller, with said magnetic drive situated outside the vessel. Alternatively, the driving means can be a positive displacement pump integrated inside the vessel. Another option can be an external pumping circuit.

In embodiments, at least one sensor element of a sensor for measuring at least one culture parameter of the cell culture may be present as a part of said cell culture device, with said sensor element being situated in said culture vessel. The sensor element may be an electrode arrangement of at least one measuring electrode. In particular, the at least one measuring electrode may be in contact with the culture medium and preferably arranged in the cell culture zone (in other words, it is preferably arranged so as to perform its measurement in the cell culture zone). In embodiments of the first aspect of the invention the electrode arrangement may be situated in a pencil-shaped probe, a wafer probe, a patch probe or it may be an electrode arrangement with its electrode(s) (e.g. its at least two or at least four measuring electrodes) integrated in the culture vessel material; e.g. on or in a cell culture substrate within the culture zone or in other words in contact with a cell culture substrate present in the culture zone (e.g. on a wall of said cell culture zone, directed toward said cell culture zone). All these embodiments of the electrode arrangement are suitable for measuring the culture parameters. With a sensor containing an electrode arrangement (which can be a simple electrode arrangement) and appropriate measuring equipment, any typical culture parameter of the cell culture can be measured, especially biomass (i.e. cell density) if an arrangement of at least four measuring electrodes is provided. In particular, the sensor may be a cell density sensor for measuring the cell concentration of the cell culture, which reflects the cell density (also referred to as biomass). The cell density sensor (biomass sensor) is preferably situated in the cell culture zone. When the cell density is measured, it is preferably determined by electrical impedance analysis or electrical impedance spectroscopy using an electrode arrangement of at least four measuring electrodes to perform a four-point-probe-measurement.

Culture parameters can be, amongst others, dissolved oxygen partial pressure, pH value, temperature and cell concentration.

As mentioned above, one problem existing in the prior art is the impossibility of manufacturing devices which are, on one hand, disposable and inexpensive (e.g. made of plastic), and on the other hand, able to permit a valid cell density measurement even in conditions where the culture vessel is deformed before or during the measurement (mechanical shock, gas overpressure in the culture vessel, . . . ). The following first and second particular embodiments represents two alternative ways of solving this problem. Any features described hereabove for the first aspect of the present invention can of course be combined with the features described in the more particular embodiments below and in particular with the features of the first, second and third particular embodiment of the first aspect.

In a first particular embodiment of the first aspect, the culture vessel may be a disposable culture vessel. In this first particular embodiment, the culture vessel preferably comprises at least one external wall made of a material having a Young modulus E of less than 50 GPa. Such materials include for instance polymeric materials which are easy to form as a vessel and lead to relatively inexpensive (and therefore disposable) vessels in comparison to the glass or steel vessels used in the prior art. Preferably, the cell-culture device further comprises at least one sensor element. The sensor element may be a cell-density sensor such as for instance an electrode arrangement of at least two and preferably at least four measuring electrodes. The sensor element is preferably situated in the culture zone of the vessel. For instance, it can be arranged on any surface inside the vessel and preferably on the inner side of an external wall of the vessel directed toward the cell culture zone and in contact with said cell culture zone. For instance, this electrode arrangement may be a patch probe or an electrode arrangement with its at least four measuring electrodes integrated in the vessel material (e.g. integrated on a wall of said cell culture zone, directed toward said cell culture zone). Optionally, said at least four measuring electrodes may be metal electrodes sputtered and/or plated on any surface inside of the vessel and preferably on the inner side of an external wall of the vessel or on a wall of said cell culture zone, directed toward said cell culture zone. Advantageously, the cell culture device may further comprise at least one driving means for driving the flow of the culture medium within the culture vessel and through the cell culture zone. Optionally, at least part of the medium-transfer zone may be surrounded by the cell-culture zone and the driving means may be in said part of said transfer zone which is surrounded by said cell culture zone. Alternatively, the driving means may be present in a bottom zone, in communication with the cell culture zone via a semi-permeable wall.

A preferred cell-culture device according to the first particular embodiment of the first aspect of the present invention may comprise:
   a disposable culture vessel comprising at least one external wall made of a material having a Young modulus E of less than 50 GPa, in which there is situated at least one cell culture zone and at least one cell-free medium-transfer zone, allowing a flow of a culture medium between the cell-culture zone and the transfer zone, and
   at least one sensor element of a cell-density sensor wherein said sensor element is situated in the culture zone of said vessel,
wherein the sensor element is an electrode arrangement of at least four measuring electrodes arranged on one of the walls delimiting the cell-culture zone, directed towards the cell-culture zone. For instance, the electrode arrangement could be arranged on the inner side of an external wall of the vessel (case of FIG. 1) or on either the inner or the outer side of an internal wall of the vessel (case of FIG. 3).

The first particular embodiment of the first aspect of the present invention solves the problem of cell density measurement in a disposable culture vessel having at least one wall of low rigidity by having a sensor element situated in the culture zone, arranged on a wall delimitating said cell culture zone (e.g. on the inner side of an external wall of the vessel) directed towards the cell culture zone. In this embodiment, the sensor is not a pencil-shaped probe. The sensor element is not extending outside of the culture vessel and has no rigid extensions extending outside of the culture vessel. It is therefore less prone to accidental shock or movements that could be initiated by mechanical forces originating outside of the culture vessel and applied to the sensor element if it was extending outside of the culture vessel. In this embodiment, the sensor element is protected within the culture vessel by being situated within the culture zone, arranged on a wall delimitating the cell culture zone (e.g. on the inner side of the vessel) directed toward the cell culture zone.

An alternative solution to this same problem is presented herebelow in a second particular embodiment of the first aspect of the present invention.

In a second particular embodiment of the first aspect, the culture vessel may be a disposable culture vessel. Preferably, the culture vessel may comprise at least one external wall made of a material having a Young modulus E of less than 50 Gpa. Preferably, the cell culture device further comprises at least one sensor element. The sensor element is preferably at least partly situated in the culture zone of the vessel, preferably not in direct contact with the casing of the vessel. For instance, it can be situated in (the heart of) the fixed bed and not in direct contact with any wall (neither an external wall, nor an internal wall). Preferably, the culture device comprises means for decoupling movements of the walls from movements of the sensor element. In other words, means for absorbing displacements of said at least one external wall so that displacements of said wall are decoupled to displacements of said sensor element. Preferably, the culture device comprises means for absorbing displacements of external walls made of a material having a Young modulus E of less than 50 Gpa so that a displacement of such a wall does not result in a displacement of the sensor element. In embodiments, the means for absorbing displacements comprise or are a flexible element connecting the external wall made of a material having a Young modulus E of less than 50 Gpa with the sensor element (e.g. a bellows). Preferably, the sensor element is connected to a measuring equipment via a non-rigid or wireless transmittal connection. A non-rigid transmittal connection is less likely to transmit mechanical energy to the inside of the disposable culture vessel. It is therefore also less likely to disturb the fixed bed packing into the cell culture zone and, consequently, less likely to change the local cell density within the cell culture zone. In embodiments of the present invention, non-rigid may have the meaning of flexible, yielding or loose.

As used herein and unless stated otherwise, the term "A is decoupled from B" means that an action on A does not leads to an action on B. For instance, if the movement or displacement of A is decoupled from the movement or displacement of B, it means that if A moves or is displaced, B will not move or be displaced. A will be said to be decoupled from B if this holds true for at least some displacements or movements, e.g. displacements or movements up to 15 mm, up to 10 mm or up to 5 mm.

Advantageously, the cell culture device may further comprise at least one driving means for driving the flow of the culture medium within the culture vessel and through the cell culture zone. Optionally, at least part of the cell-free medium transfer zone is surrounded by the cell culture zone and the driving means may be in said part of said transfer zone which is surrounded by said cell culture zone. Alternatively, the driving means may be present in a bottom zone, in communication with the cell culture zone via a semi-permeable wall.

A preferred cell culture device according to the second particular embodiment of the first aspect of the present invention may comprise:
- a disposable culture vessel comprising at least one external wall made of a material having a Young modulus E of less than 50 GPa, in which there is situated at least one cell culture zone and at least one cell free medium transfer zone, allowing a flow of a culture medium between the cell culture zone and the transfer zone, and
- at least one sensor element (11) at least partly situated in the cell culture zone (5) of said vessel and not in direct contact with the casing (3) of said vessel, wherein said cell culture device (1) further comprises means for absorbing displacements of said at least one external wall so that a displacement of said wall does not result in a displacement of said sensor element.

In a third particular embodiment of the first aspect, at least part of the cell free medium transfer zone may be surrounded by the cell culture zone and the cell culture device further comprises at least one driving means for driving the flow of the culture medium within the culture vessel and through the cell culture zone. For instance, said cell free medium transfer zone may be internal to the cell culture zone and in medium communication with said cell culture zone via a top zone of the vessel, allowing the circulation of the culture medium. This allows the device to be more compact. Preferably the cell free transfer zone is delimited by one or more semi-permeable walls. No bottom zone is needed in this embodiment. This driving means is preferably in said part of said transfer zone which is surrounded by said cell culture zone. Also in this embodiment, the culture vessel may be a disposable culture vessel. Preferably, the culture vessel comprises at least one external wall made of a material having a Young modulus E of less than 50 Gpa.

Advantageously, the cell culture device may further comprise at least one sensor element. In a first alternative, the sensor element may be a cell-density sensor such as for instance an electrode arrangement of at least four measuring electrodes. The sensor element may be preferably situated in the cell culture zone of the vessel. For instance, it can be arranged on one of the walls delimiting the cell culture zone (e.g. on the inner side of an external wall of the vessel) directed toward the cell culture zone. For instance, this electrode arrangement may be a patch probe or an electrode arrangement with its at least four measuring electrodes integrated in the vessel material (e.g. on or in a wall of said cell culture zone, directed toward said cell culture zone. Optionally, said at least four measuring electrodes may be metal electrodes sputtered and/or plated on one of the walls delimiting the cell culture zone (e.g. on the inner side of an external wall of the vessel). In a second alternative, the sensor element may be at least partly situated in the culture zone of the vessel, preferably not in direct contact with the casing of the vessel, said casing having at least one external wall made of a material having a Young modulus E of less than 50 Gpa and the culture device comprises means for absorbing displacements of these external walls made of a material having a Young modulus E of less than 50 Gpa so that a displacement of such a wall does not result in a displacement of the sensor element. Or in other words, it comprises means for decoupling movements of the walls from movements of the sensor element.

In embodiments, the means for absorbing displacements comprise or are a flexible element connecting the external wall made of a material having a Young modulus E of less than 50 Gpa with the sensor element (e.g. a bellows). Preferably, the sensor element is connected to a measuring equipment via a non-rigid or wireless transmittal connection.

A preferred cell culture device according to the third particular embodiment of the first aspect of the present invention may comprise:
- a culture vessel in which there is situated at least one cell culture zone and at least one cell free medium transfer zone, allowing a flow of a culture medium between the cell-culture zone and the transfer zone, wherein at least part of said transfer zone is surrounded by said cell culture zone, and
- at least one driving means for driving the flow of the culture medium within the culture vessel and through the cell culture zone, wherein said driving means is in said part of said transfer zone which is surrounded by said cell culture zone.

As an optional feature of any embodiment of the first aspect of the present invention, the culture vessel may be made of a material having a Young modulus E of less than 50 GPa. In other words, the whole vessel may be made of such a material. This permits an inexpensive and therefore disposable culture vessel to be obtained.

As another optional feature of any embodiment of the first aspect of the present invention, the material may be sterilisable (heat sterilisable and/or gamma irradiation sterilisable). By sterilisable, it is meant that the material can withstand steam heating or gamma irradiation without deforming or losing its main mechanical properties. This is advantageous as it permits the inactivation of all fungi, bacteria, viruses and also bacterial spores.

As another optional feature of any embodiment of the first aspect of the present invention, the material may be electrically insulating.

As another optional feature of any embodiment of the first aspect of the present invention, the material may be a thermoset or a thermoplastic material. Such polymeric materials permit a culture vessel to be obtained which is less expensive and therefore disposable. For instance, the material may be selected from the group consisting of polypropylene, polycarbonate, polyester, e.g. polyethylene terephthalate, and polymethylmethacrylate.

As an optional feature of any embodiments of the present invention, the cell culture zone and the cell-free medium-transfer zone may be separated by one or more (semi-permeable) walls permeable to the fluid, but not permeable to the cells (or their carriers/microcarriers when culture carriers or microcarriers are present in the cell culture zone). For instance, one or more of said walls may be provided with one or more orifices or may be a membrane permeable to the medium, but not to the cells. The use of such a membrane is preferred when the device is used for suspension cell culture (without carriers or microcarriers).

When cell-free top and bottom zones are present above and under the cell-culture zone, the semi-permeable walls are preferably 1) the wall adjacent to both the cell-culture zone and the cell-free top zone, and 2) the wall adjacent to both the cell-culture zone and the cell-free bottom zone.

When no cell-free bottom zone is present under the cell culture zone, the semi-permeable wall(s) are preferably 1) the wall adjacent to both the cell-culture zone and the cell-free top zone, and 2) the side wall (s) adjacent to both the cell-culture zone and the cell-free zone (e.g. the wall(s) delimiting laterally the cell free zone).

As another optional feature of any embodiment of the first aspect of the present invention wherein at least one electrode is present as a sensor element, the electrode may be a metal electrode (or the at least four electrodes are metal electrodes) sputtered and/or plated directly on an internal surface of a vessel component (e.g. on a wall of said cell culture zone, directed toward said cell culture zone or on the inner side of an external wall of the vessel). Preferably said metal electrodes may be noble metal electrodes, such as but not limited to the noble metals gold and platinum.

As another optional feature of the first or second particular embodiment of the first aspect of the present invention, when at least one driving means is present, the driving means may be situated in the disposable culture vessel.

As another optional feature of the first or second particular embodiment, when at least one driving means is present for driving the flow of the culture medium (M) within the culture vessel and through the cell culture zone, said at least one driving means (16) may be situated outside the disposable culture vessel (see FIG. 11).

As another optional feature of any embodiment of the first aspect of the present invention, when driving means are present, the driving means may comprise an impeller driven by a drive motor (or comprise an impeller suitable for being driven by a drive motor), wherein said impeller is situated in the vessel. For instance, the drive motor may be a magnetic drive and the impeller may be a magnetic impeller, wherein said magnetic drive is situated outside the vessel.

As another optional feature of any embodiment of the first aspect of the present invention, when driving means are present, the flow of the culture medium may be a circulation through the transfer zone and the cell-culture zone driven by the driving means.

As another optional feature of the first or the second embodiment of the first aspect of the present invention, said transfer zone may be internal to the cell culture zone and in medium communication with said cell culture zone via a top zone and a bottom zone of the vessel, allowing the circulation of the culture medium.

As another optional feature of the first or second embodiment of the first aspect of the present invention, when an impeller and a bottom zone are present, the impeller may be situated in said bottom zone, allowing a circulation of the culture medium from the bottom zone to the top zone through said cell-culture zone, and back from the top zone to the bottom zone through said cell-free medium transfer zone.

As another optional feature of any embodiment the first aspect of the present invention, the culture vessel may comprise at least one gas inlet orifice and one gas outlet orifice. In this way, it is possible to enrich the ambient atmosphere of the culture vessel with oxygen for example, as the oxygen is consumed by the cells. The liquid medium has a surface area that can exchange oxygen. This can also avoid a sparging system that requires a tube connection through a device wall. It is also possible to supply the ambient atmosphere with other gases, for example by adding $CO_2$ in order to modify the pH value, or any other gas generally used in cell culture. The outlet orifice allows installation of an overpressure valve to prevent overpressures and/or to discharge gas with a low oxygen content or simply part of the gas of the ambient atmosphere in order to reduce the ambient pressure of the device. Also, provision is made to be able to close off or "throttle" this gas outlet in the case where a slight overpressure is desirable. The gas inlet can be situated or connected to the top zone, to the bottom zone, to the culture zone or to the transfer zone of the culture vessel.

As an optional feature of any embodiment of the present invention, the culture device may be adapted for use with gas overpressure in said disposable culture vessel. In embodiments of the first aspect of the present invention, the overpressure is from 10 mbar to 100 mbar. Light overpressure is a direct consequence of gas flow rate through the gas phase of the cell culture device, which creates a pressure drop through the outlet filter; optionally, one can implement a controlled overpressure of 10 mbar to 100 mbar, to avoid any contamination (bacteria for example) by potential leakages of the cell culture device.

As another optional feature of any embodiment of the first aspect of the present invention, when a sensor element is present (e.g. a sensor element of a cell-density sensor), the cell-culture device may further comprise or can be used with at least one controller device connected (or coupled or couplable) to the sensor element (or to an output of the sensor element) for controlling at least one culturing factor (culture factor control) depending on the signal or culture parameter (e.g. cell density) measured by said sensor element. For example, when driving means are present, the controller may provide a speed signal for driving means so as to regulate the speed of circulation of the medium. Other culture factors that can be controlled in accordance with the output of the sensor element include, amongst other things: the quantity of different gases in the vessel, e.g. the controller device could, for example, inject or control the injection of gas such as $CO_2$ into the vessel according to the signal such as pH value obtained by the sensors or any other type of regulation generally used in this type of culture. It could for example modulate or control the modulation of a quantity of oxygen to be injected into the gaseous atmosphere according to the value of the dissolved oxygen partial pressure present or the quantity of dissolved oxygen consumed by the cells.

As another optional feature of any embodiments of the first aspect of the present invention, the cell culture device may further comprise a first oxygen or oxygen partial pressure probe located in the at least one cell-free medium-transfer zone and a second oxygen or oxygen partial pressure probe in the cell culture zone. This is advantageous as it permits the value of the dissolved oxygen consumption rate by the cells to be determined.

As another optional feature of any embodiments of the present invention, when at least one electrode is present, the surface of each electrode may be made of a noble metal.

As another optional feature of the first or the second particular embodiment of the present invention, at least part of said transfer zone may be surrounded by said cell culture zone.

As another optional feature of the first or the second particular embodiment of the present invention, when driving means are present and when at least part of the transfer zone is surrounded by the cell culture zone, said driving means may be in said part of said transfer zone which is surrounded by said cell-culture zone.

As another optional feature of the first or the second particular embodiment of the present invention, the device may be adapted so as to permit the culture medium to flow from the bottom to the top through the culture zone.

As another optional feature of the first or the second particular embodiment of the present invention, the impeller may be situated in said bottom zone, allowing a circulation of the culture medium from the bottom zone to the top zone through said cell-culture zone, and back from the top zone to the bottom zone through said transfer zone.

As another optional feature of any embodiment of the present invention, the vessel may comprise heating and/or cooling means, designed to heat and/or cool the transferred culture-medium. When a bottom zone is present, this heating and/or cooling means can advantageously be situated in said bottom zone. Naturally, the transfer zone can also comprise this heating and/or cooling means. The heating means can be an electrical element, an electrical coil or any other heating means generally used in the field of cell culture, such as for example a thermostatically controlled double jacket. The cooling means may be any suitable miniaturisable cooling means such as a Peltier element.

In a second aspect, the present invention relates to a method of culturing cells, using a cell culture device according to any embodiment of the first aspect wherein a sensor element of a cell-density sensor is present and wherein the cell density of the cell culture is measured by the sensor element.

As an optional feature of any embodiment of the second aspect of the present invention, in addition of the measurement of the cell density, at least one culturing factor may be determined and/or controlled depending on said measured cell density. Preferably, the culturing factor is selected from temperature, an introduction rate of a component to be introduced in said cell culture device, a viral infection time, an induction time for a recombinant process, a harvest time or harvest period (e.g. of a metabolic product such as a virus, a protein, lactate or ammonium). For instance, said component may be selected from the group consisting of a gas (e.g. oxygen, nitrogen, air, carbon dioxide, . . . ), a pH modifier, oxygen, a metabolic product or a product to be metabolized. The metabolic product may, for instance, be lactate, ammonium, a virus or a protein (e.g. a recombinant protein or a monoclonal antibody). The product to be metabolized may, for instance, be carbonates or glucose.

Another object of the invention is the use of the culture device according to the invention for cell culture in suspension on microcarriers or on carriers in combination with a bottom wall and a top wall (e.g. wherein the carriers or microcarriers are confined in the culture zone at least partly delimited by a bottom wall and a top wall and separated from the cell free medium transfer zone by said bottom wall and said top wall), each wall being provided with orifices allowing a transfer of culture medium essentially free from cells. Indeed, when the device according to the invention is used with culture carriers or microcarriers, the carriers or microcarriers are preferably confined in said culture zone. When the device is used for suspension cell culture, and therefore without carriers or microcarriers, the wall provided with an orifice is preferably a membrane permeable to the medium but not permeable to the cells.

The invention also relates to the use of the culture device according to the invention for producing recombinant products, viruses, metabolites and the like.

Yet another object of the invention relates to a method of culturing cells, using one of the aforementioned cell culture devices, wherein the culture parameter of the cell culture is measured by the sensor element, and at least one culturing factor is controlled or regulated depending on said measured culture parameter. The culture parameter of the cell culture may be measured by an electrode arrangement of at least one measuring electrode of the sensor. Culture parameters means, amongst other things, biomass or cell density, the dissolved oxygen partial pressure, oxygen content, the pH value, the temperature, certain concentrations of nutriments, such as lactate, ammonium, carbonates, glucose or any metabolic product or product to be metabolised which could for example reflect the cell density. The cell density (biomass density) is preferably determined by electrical impedance analysis or electrical impedance spectroscopy using the arrangement of the measuring electrode. According to the measured culture parameter (the signal) like the cell density for example, the quantity of oxygen in a volume of gas inside the vessel may be regulated or the speed of the driving means may be controlled. By realizing this kind of culture factor control a device can be realized with a vessel volume of about 10 milliliters to 250 liters, and a ratio between the cell-free culture medium volume and the volume of the cell culture zone of about 0.5:1 to about 10:1, preferably less than 2:1.

BRIEF DESCRIPTION OF THE DRAWINGS

In the drawings, which illustrate embodiments of the invention.

DESCRIPTION OF THE PREFERRED EMBODIMENTS

Figure 1:
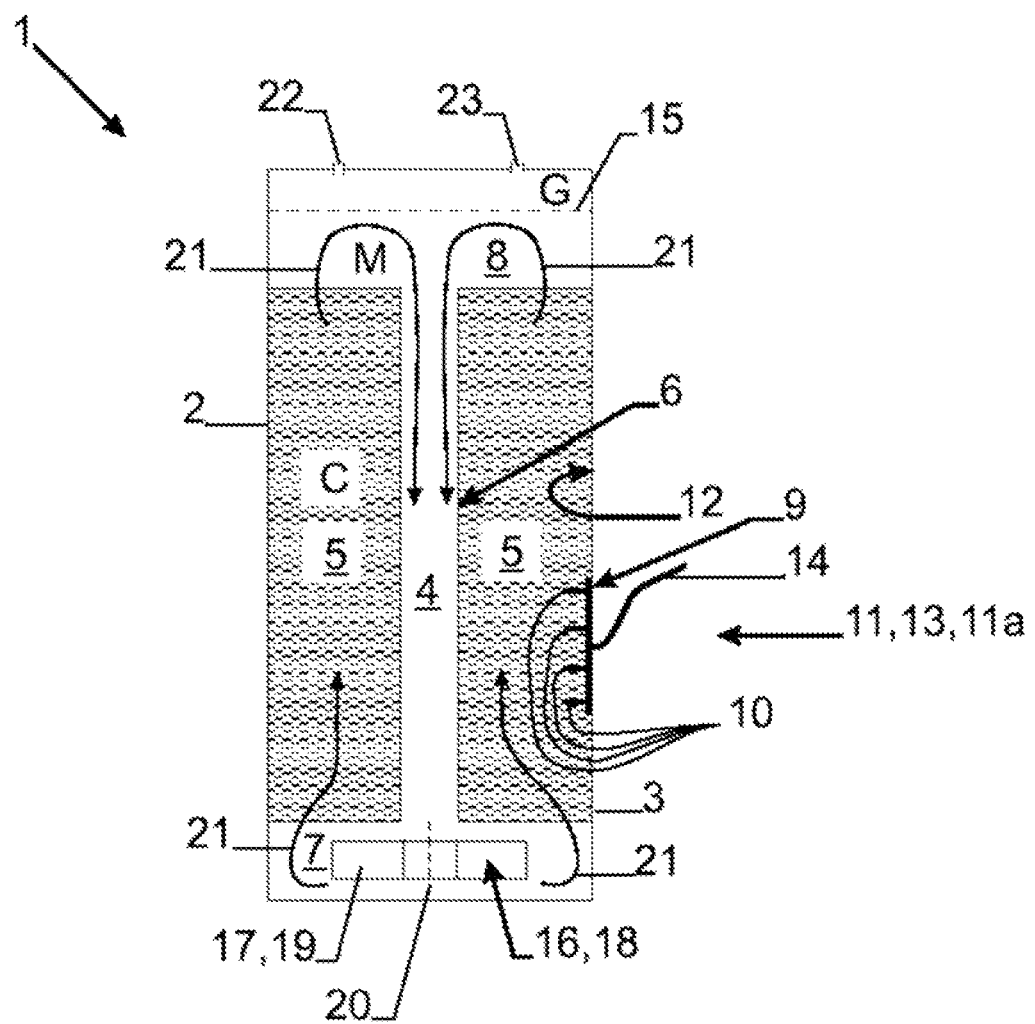
FIG. 1 is a vertical sectional view of a cell culture device according to the first particular embodiment of the first aspect of the invention.

The drawings described are only schematic and are non-limiting. In the drawings, the size of some of the elements may be exaggerated and not drawn to scale for illustrative purposes. The mere fact that certain measures are recited in mutually different dependent claims does not indicate that a combination of these measures cannot be used to advantage. Any reference signs in the claims should not be construed as limiting the scope.

Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the figures below, a part of the cell-free medium transfer zone has usually been assigned a numeral "4". However, the place of this numeral on the figures is illustrative only as it must be well understood that the cell-free medium transfer zone represents the entirety of the culture vessel volume minus the cell culture zone. In other words, the top and bottom zones, when present, are also part of the cell-free transfer zone. Similarly, the recipient shown on the right side of FIG. 11 as well as the tubing linking it to the cell culture zone 5 are part of the cell-free medium transfer zone.

As can be seen in FIG. 1, a culture device 1 according to a variant of the first particular embodiment of the first aspect of the present invention comprises a substantially vertical and cylindrical culture vessel 2, although other forms can also be envisaged according to the invention. Said vessel 2 is made of an electrically insulating material. The vessel 2 comprises a vessel casing 3 and at least four internal zones in medium communication with one another. From the centre of the vessel 2 radial towards the outside, the vessel comprises a cell-free transfer zone 4 and a cell-culture zone 5 separated by a tube 6. Both of said zones 4, 5 border with their lower sides on a bottom zone 7 and with their upper sides on a top zone 8 of the vessel 2, respectively. The cell culture zone 5 comprises a cell culture of cells anchored to a suitable cell culture substrate or in suspension on carriers/microcarriers in combination with a bottom wall and a top wall (identified by the letter C), each wall being provided with orifices allowing a transfer of culture medium essentially free from cells (not shown). An electrode arrangement 9 with at least one and optionally four measuring electrodes 10, which is a sensor element of a sensor 11, is arranged on the inner side 12 of the vessel casing 3 directed towards the cell culture zone 5. Said electrode arrangement 9 is situated on a patch probe 13 and fabricated by plating or sputtering a noble metal (in particular platinum) onto contact pads of the patch probe 13 at the inner side 12 of the vessel casing 3. The electrodes 10 are connected to measuring equipment (not shown) of the sensor 11 through the vessel casing (exterior walls) 3 by a cable 14. Said sensor 11 is a cell density sensor 11a for measuring the cell concentration of the cell culture, which reflects the cell density in the cell-culture zone 5.

The culture medium is shown by the letter M. The bottom zone 7, the transfer zone 4 and the cell culture zone 5 are completely filled with culture medium M, the top zone 8 is filled partially up to the fluid level 15. Said top zone 8 encloses a volume of gas (identified by the letter G) consisting of the ambient atmosphere of the culture vessel 2. This volume of gas can also constitute an oxygenation zone for the culture medium M. As an oxygenation or aeration zone is provided this embodiment does not require a separate sparging device that enters a device wall through a tube from the exterior i.e. from outside the culture vessel. Nevertheless, should this be necessary, a sparging device can be accommodated inside the transfer zone 4.

The culture vessel 2 comprises a driving means 16 in its bottom zone 7. Said driving means 16 contains an impeller 17. The driving means 16 is preferably adapted for activation without a penetration through a device wall. Hence the device of the present embodiment does not need an external circuit including a pump, either a hand pump or a driven pump and a fluid connection through a wall of the device. The driving means 16 is, in this preferred embodiment, composed of a magnetic device 18, for example a magnetic bar or a magnetic impeller 19 in rotation about a central rotation axis 20, real or virtual. The magnetic device 18 is driven by a rotary magnetic drive motor external to the culture vessel 2 and which is not shown here. The magnetic device 18 functions as a centrifugal pump, that is to say the medium is sucked from the transfer zone 4 into a relatively central part of the magnetic device 18 by the flow of the medium created by the magnetic device 18 and the medium is propelled outwards with respect to the central point. The magnetic device 18 is driving a circulation (arrows 21) of the culture medium M from the bottom zone 7 to the top zone 8 via said cell culture zone 5, and back from the top zone 8 to the bottom zone 7 via said transfer zone 4. The culture vessel 2 comprises one gas inlet orifice 22 and one gas outlet orifice 23.

Figure 2:
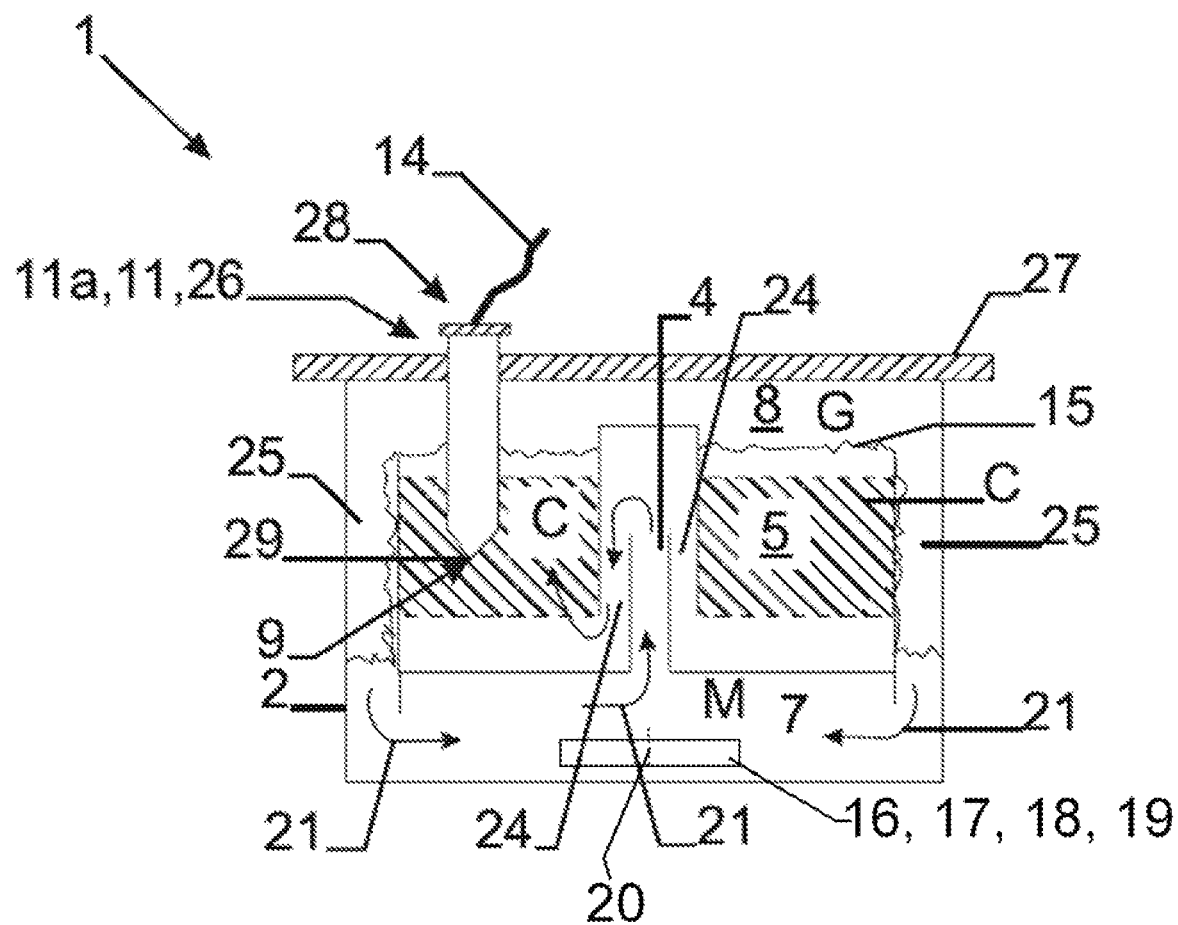
FIG. 2 is a vertical sectional view of a cell culture device in another embodiment of the invention.

In the embodiment shown in FIG. 2, the vessel 2 of the culture device 1 also comprises a second culture-medium transfer zone 24 and a third culture-medium transfer zone 25. Said second transfer zone 24 is a zone internal to said cell culture zone 5 and external to said first transfer zone 4 and said third transfer zone 25 is a zone external to said cell culture zone 5, said second transfer zone 24 being in medium communication with the transfer zone 4 and cell culture zone 5 and said third transfer zone 25 being in medium communication with the culture zone 5 and with the medium transfer zone 3 via the culture medium driving means 16. The driving means 16 allows a circulation of the culture medium from bottom to top in said cell culture zone 5.

The electrode arrangement 9 of this embodiment is part of a pencil-shaped probe 26 extending from a cover 27 of the vessel 2 to the inside of the culture zone 5. One end 28 of the pencil-shaped probe 26 is outside the vessel 2 in electrical contact with the cable 14 and the other end 29 dips with an electrode arrangement 9 into the culture medium M in the culture zone 5. Other aspects are as described previously for the first embodiment. This pencil-shaped probe is preferably replaced by an electrode arrangement according to the first or the second particular embodiment of the present invention. This can be seen on FIG. 12.

Figure 3:
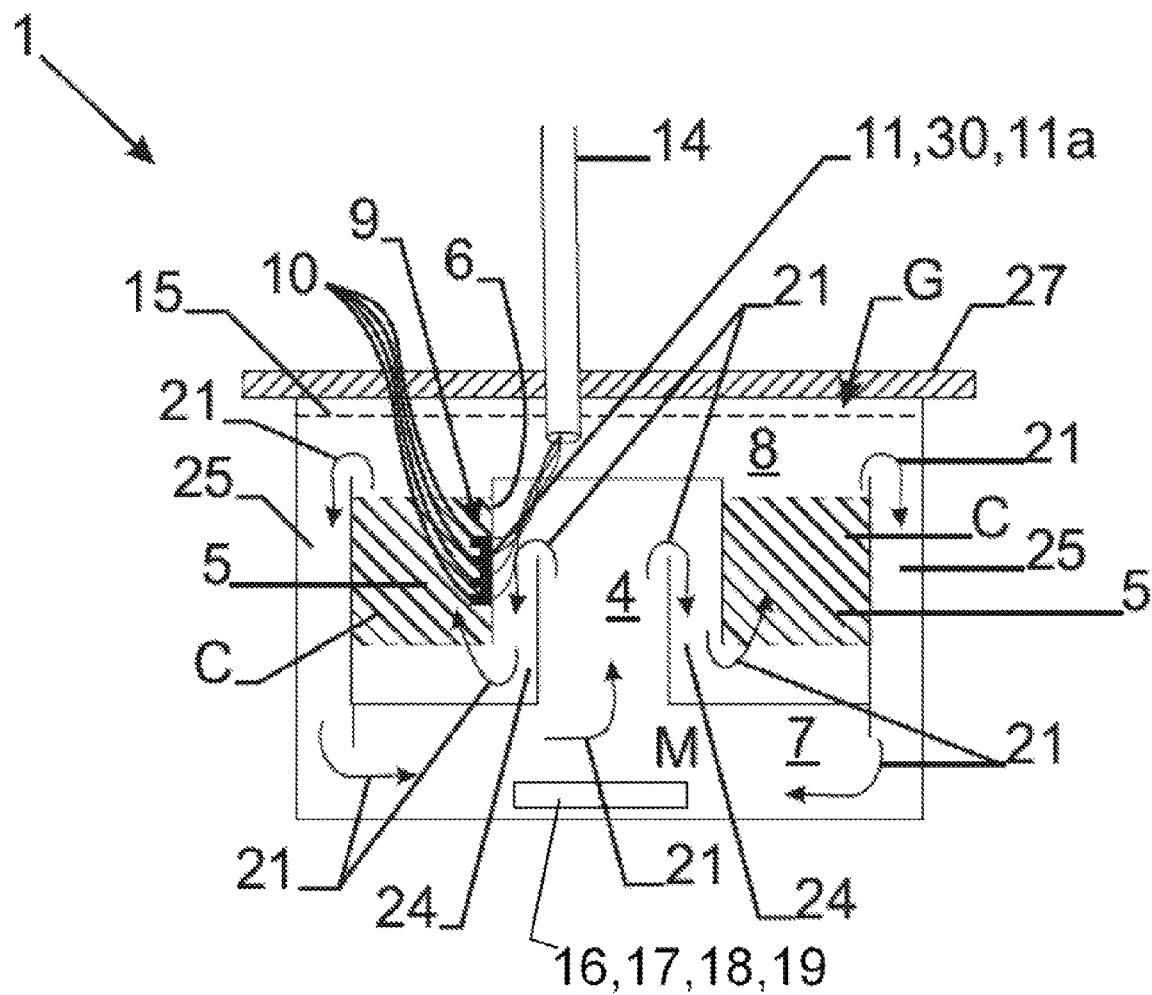
FIG. 3 is a vertical sectional view of a cell culture device according to a variant of the first particular embodiment of the first aspect of the present invention.

The embodiment shown in FIG. 3, is essentially in accordance with the embodiment of FIG. 2. However, the electrode arrangement 9 of the third embodiment is an electrode arrangement 30 of electrodes 10 integrated in the vessel material close to the cell culture zone 5, either as an alternative to or as an additional element to the sensor electrodes of the embodiment of FIG. 2. Other aspects are as for the embodiment of FIG. 1.

Figure 4:
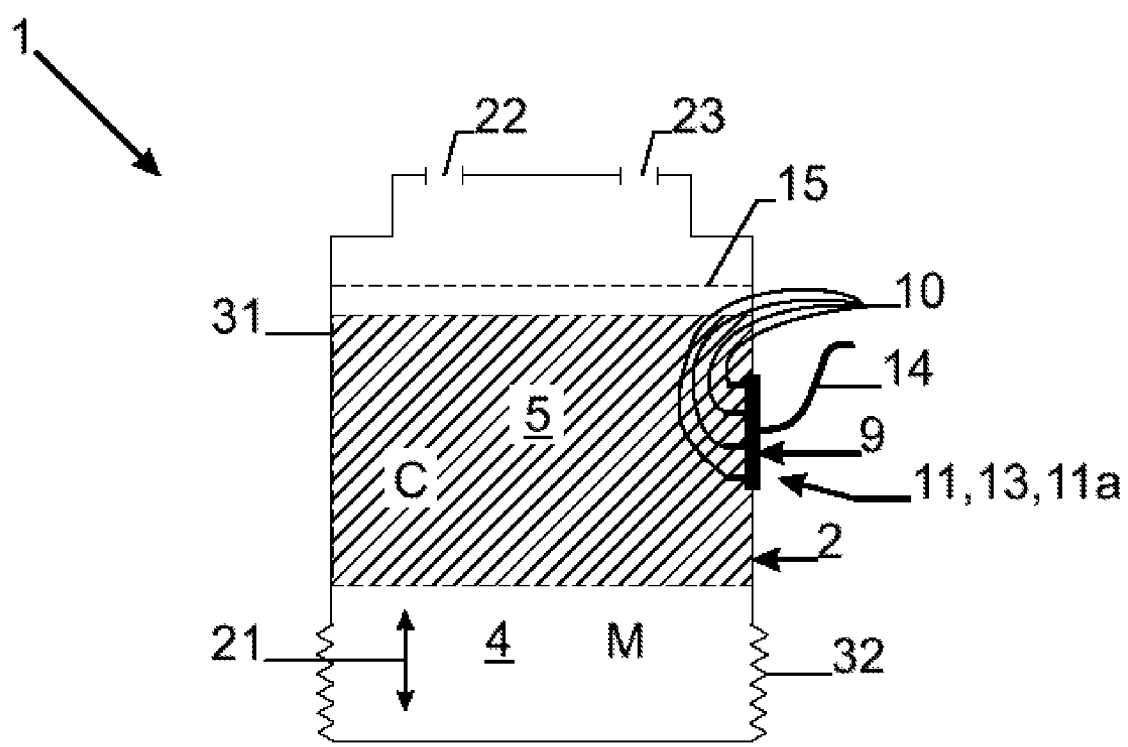
FIG. 4 is a vertical sectional view of a cell culture device according to another variant of the first particular embodiment of the first aspect of the present invention.

FIG. 4 illustrates a further embodiment of the invention. The culturing device 1 is a bioreactor with a first chamber 31 containing the cell culture zone 5 with cell-culture substrate means C for cell attachment and a second chamber 32 connected to the first chamber 31. Said second chamber 32 has a compressible component in the form of a bellow that can be compressed and extended and includes the transfer zone 4 and the driving means (compressible component itself) to facilitate the culture medium M to flow in a see-saw motion freely between the first and the second chamber 31, 32 through the cell culture zone 5. The cover of the vessel 2 comprises an air filter (not shown) and at least one opening or inlet/outlet orifices 22, 23. The electrode arrangement 9 is situated on a patch probe 13 arranged at the inner side of the vessel casing (exterior walls) in the cell culture zone 5. In a variant, the electrode arrangement 9 is an electrode arrangement with its electrodes 10 integrated in a culture zone section of the vessel 2 along the entire circumference at the inner side of the vessel casing. In another variant, the electrode arrangement 9 is an electrode arrangement with its electrodes 10 integrated in the heart of the fixed bed, and not solidarized to any wall, neither an external wall nor an internal wall of the vessel.

Figure 5:
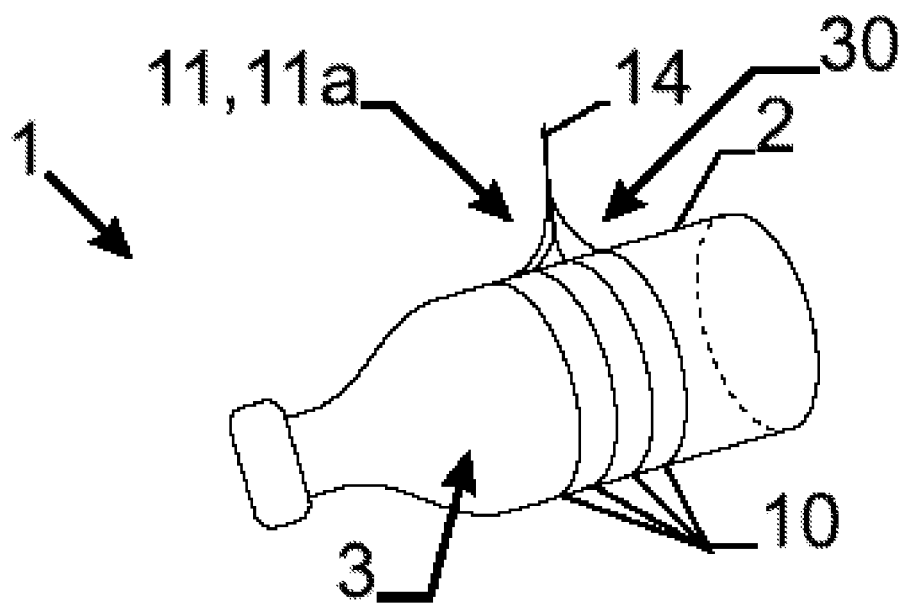
FIG. 5 is a perspective view of a cell culture device according to yet another variant of the first particular embodiment of the first aspect of the present invention.

FIG. 5 illustrates a further embodiment of the invention. The culture device 1 is of the "roller bottle"-type. The measuring electrode arrangement 9 is an electrode arrangement 30 with its electrodes 10 integrated in a middle section of the bottle along its entire circumference at the inner side 12 of the bottle wall (vessel casing 3) close to the cell culture zone (not shown). The vessel 2 of the device is made of an electrically insulating material.

The culturing device 1 can of course be a bioreactor of any other known type (for example "T-flask"-type) in combination with an electrode arrangement 9 of at least one measuring electrode 10 for measuring at least one culture parameter of the cell culture as described above, e.g. with said electrode arrangement 9 arranged in the vessel and advantageously arranged in the cell culture zone of the vessel.

Each kind of sensor 11 with the electrode arrangement 9 can be used to measure culture parameters of the cell culture. In particular, the electrode arrangement 9 can be used in a cell density sensor 11a to determine the cell density (biomass density) by electrical impedance analysis or electrical impedance spectroscopy. This is particularly preferred as biomass sensors tend to be large in size and the integration of electrodes onto or into internal components of the culture device saves space. According to the measured culture parameters like the cell density for example, the culturing factors like the medium flux or the quantity of oxygen in a volume of gas inside the vessel can be controlled. By realizing this kind of culture factor control one could realize a device with a vessel volume of 1000 milliliters or less and a ratio between the cell medium volume and the volume of the cell culture zone of about 0.5:1 to about 10:1, preferably less than 2:1.

In particular, the device can comprise or can be used with at least one controller device coupled or couplable to an output of the sensor and adapted for controlling at least one culturing factor (culture factor control) depending on said culture parameter. Culture factors that can be controlled in accordance with the output of the sensor include, amongst other things: the speed of the driving means and the quantity of different gases in the vessel. The controller device could, for example, provide a speed signal to the driving means to control the rate of circulation of the medium. The controller device could for example inject or control the injection of $CO_2$ into the vessel according to the pH value obtained by the sensors or any other type of regulation generally used in this type of culture. It would for example modulate or control the modulation of a quantity of oxygen to be injected into the gaseous atmosphere according to the value of the dissolved oxygen partial pressure present or the quantity of dissolved oxygen consumed by the cells. This kind of culture factor control, allows a device with a vessel volume of 10 milliliters to 250 liters, and a ratio between the cell-free culture medium transfer zone volume and the volume of the cell culture zone of about 0.5:1 to about 10:1 to be realized. The cell-free culture medium transfer zone volume being the total volume of the culture vessel minus the volume of the cell culture zone.

A further embodiment of the present invention will be described with reference to FIG. 2, which can be included in other embodiments, e.g. that of FIG. 3 and represents an independent invention. The medium as it travels through the cell culture will lose oxygen as this is used up by the living cells. If the concentration of oxygen at the end of the trajectory of the medium is too low, an attempt can be made to compensate for this by increasing the speed of action of the impeller and hence the throughput of the medium. However, increasing the speed of the medium may or may not increase the amount of oxygen in the medium as the residence time in the oxygenation zone 25 may be reduced. Thus it may be necessary to vary the oxygen or carbon dioxide or nitrogen mix that is supplied to the cell culture device combined with the speed of the impeller. To allow control of these factors and to obtain optimum results it is preferred to have probes, such as oxygen concentration or oxygen partial probes introduced into the medium at two places within the device. A first probe for example can be placed in the first transfer zone 4 after the medium has passed through the oxygenation zone 25. A second probe can be placed in the medium at the top of cell culture zone 5. The two probes can extend from the cover 27 of the vessel 2 to the inside of the culture zone 5 and the first transfer zone 4 respectively. The two probes may be placed at other positions of the cell provided they give some indication of the oxygen concentration or oxygen partial pressure after oxygenation and after passing through the cell culture, respectively. All other aspects are as for the first embodiment and other embodiments described above.

These two probes form part of an oxygen concentration or oxygen partial pressure measuring unit. This unit is able to measure the difference in oxygen concentration or oxygen partial pressure of the medium between a first position after oxygenation and a second position after passing through the cell culture as well as optionally measuring a value related to the absolute oxygen concentration or oxygen partial pressure at these positions. The controller can be adapted to receive the signals from the first and second probe and to control the speed of the impeller and/or the amount of any of oxygen, carbon dioxide or nitrogen in the gas supplied to the culture device in order to optimise the dissolved oxygen concentration in the circulating medium. As it can be desirable to have similar conditions at all points in the cell culture, this optimisation is preferably to operate the controller such as to reduce the difference in oxygen concentration between positions after oxygenation and after passing through the cell culture, while still maintaining an adequate absolute oxygen concentration throughout the cell culture at all positions. Although in this embodiment oxygen probes have been described, other probes may be used instead to measure any relevant parameter such as a quantity of at least one gas in the cell culture device, pH value of the cell medium, biomass of the cell culture, dissolved oxygen partial pressure, temperature, concentrations of nutriments, such as lactate, ammonium, carbonates, glucose or any metabolic product or product to be metabolised which could for example reflect the cell density.

The controller may be implemented in hardware, in firmware, including FPGAs, ASICs, microprocessors or the like. A hardware solution can be be embedded into a computer or other processing device. The controller can also be implemented in software for execution on a processing engine residing in a computer or other form of processing device. Control methods of the invention can be performed by programming the steps and storing the program on computer readable media.

Figure 7:
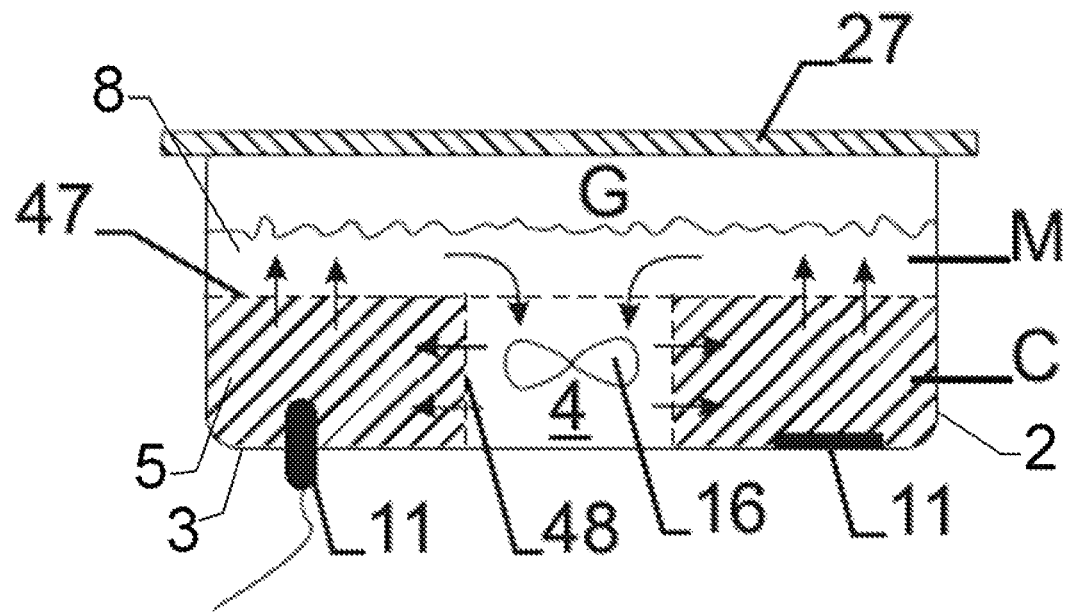
FIG. 7 is a vertical sectional view of a cell culture device according to the third particular embodiment of the first aspect of the present invention.

As can be seen in FIG. 7, a culture device according to a variant of the third particular embodiment of the first aspect of the present invention comprises a substantially vertical and cylindrical culture vessel, although other forms can also be envisaged according to the invention. Said vessel is preferably made of an electrically insulating material. The vessel comprises a vessel casing and internal zones in medium communication with one another. From the centre of the vessel radial towards the outside, the vessel comprises a cell free transfer zone 4 and a cell culture zone 5 separated by a semi-permeable tube 48. None of said zones 4, 5 border with their lower sides a bottom zone since no cell free bottom zone is present under the cell culture zone 5. Both of said zones 4 and 5 border with their upper sides on a top zone 8 of the vessel 2, respectively. The cell culture zone 5 comprises a cell culture of cells anchored to a suitable cell culture substrate or in suspension on carriers/microcarriers (identified by the letter C) in combination with a non-permeable bottom wall, a semi-permeable top wall 47 and a semi-permeable tube 48. The top wall 47 and the semi-permeable tube 48 can be made semi-permeable by being provided with orifices allowing a transfer of culture medium essentially free from cells (not shown). A sensor element 11 can be present and arranged in contact with the culture medium. When present, the probe(s) 11 are connected to measuring equipment (not shown) of the sensor through the vessel casing 3 by a cable or wireless.

The culture medium is shown by the letter M. The transfer zone 4 and the cell culture zone 5 are completely filled with culture medium M, the top zone 8 is filled partially up to a fluid level. Said top zone 8 encloses a volume of gas (identified by the letter G) consisting of the ambient atmosphere of the culture vessel. This volume of gas can also constitute an oxygenation zone for the culture medium M. As an oxygenation or aeration zone is provided this embodiment does not require a separate sparging device that enters a device wall through a tube from outside the exterior walls.

The culture vessel comprises a driving means 16 in its central transfer zone 4. Said driving means 16 contains an impeller. The driving means 16 is preferably adapted for activation without any penetration through a device wall. Hence the device of the present embodiment does not need an external circuit including a pump, either a hand pump or a driven pump and a fluid connection through a wall of the device. The driving means 16 can be, in this third particular embodiment, composed of a magnetic device, for example a magnetic bar or a magnetic impeller in rotation about a central rotation axis, real or virtual. The magnetic device may be driven by a rotary magnetic drive motor external to the culture vessel 2 and which is not shown here. The magnetic device functions as a centrifugal pump, that is to say the medium is sucked from the transfer zone 4 into a relatively central part of the magnetic device by the flow of the medium created by the magnetic device and the medium is propelled outwards with respect to the central point. The magnetic device is driving the circulation (arrows) of the culture medium M from the transfer zone 4 to the top zone 8 via said cell culture zone 5, and back from the top zone 8 to the transfer zone 4.

Figure 8:
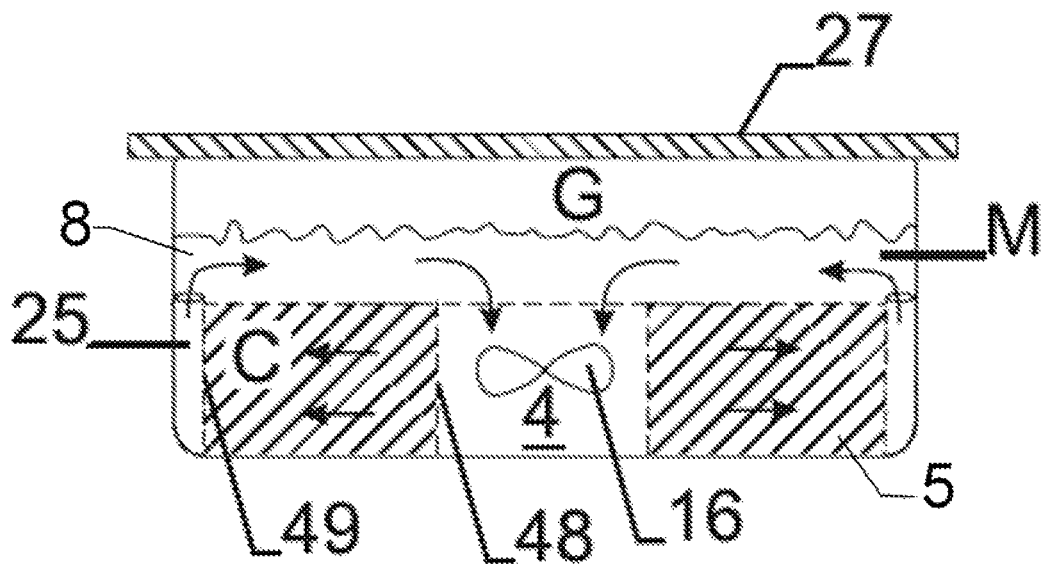
FIG. 8 is a vertical sectional view of a cell culture device according to a variant of the third particular embodiment of the first aspect of the present invention.

As can be seen in FIG. 8, a culture device according to a variant of the third particular embodiment of the first aspect of the present invention comprises a substantially vertical and cylindrical culture vessel, although other forms can also be envisaged according to the invention. Said vessel is preferably made of an electrically insulating material. The vessel comprises a vessel casing and internal zones in medium communication with one another. From the centre of the vessel radial towards the outside, the vessel comprises a cell-free transfer zone 4 and a cell-culture zone 5 separated by a semi-permeable tube 48. None of said zones 4, 5 border with their lower sides a bottom zone since no cell free bottom zone is present under the cell culture zone 5. Both of said zones 4 and 5 border with their upper sides on a top zone 8 of the vessel. The cell culture zone 5 comprises a cell culture of cells anchored to a suitable cell-culture substrate or in suspension on carriers/microcarriers (identified by the letter C) in combination with a non-permeable bottom wall, a non-permeable top wall, a semi-permeable external side wall 49 (separating the cell free transfer zone 25 from the cell culture zone 5) and a semi-permeable tube 48. The semi-permeable external side wall 49 and the semi-permeable tube 48 can be made semi-permeable by being provided with orifices allowing a transfer of culture medium essentially free from cells (not shown). A sensor element can be present as described in FIG. 7 or in any embodiment of the present invention.

The culture medium is shown by the letter M. The transfer zones 4 and 25 and the cell culture zone 5 are completely filled with culture medium M, the top zone 8 is partially filled up to a fluid level. Said top zone 8 encloses a volume of gas (identified by the letter G) consisting of the ambient atmosphere of the culture vessel. This volume of gas can also constitute an oxygenation zone for the culture medium M. As an oxygenation or aeration zone is provided this embodiment does not require a separate sparging device that enters a device wall through a tube from outside the external walls.

The culture vessel comprises a driving means 16 in its central transfer zone 4. Said driving means 16 contains an impeller. The driving means 16 is preferably adapted for activation without a penetration through a device wall. Hence the device of the present embodiment does not need an external circuit including a pump, either a hand pump or a driven pump and a fluid connection through a wall of the device. The driving means 16 can be as described in FIG. 7. The magnetic device 18 is driving a circulation (arrows) of the culture medium M from the transfer zone 4 to the top zone 8 via said cell culture zone 5, and back from the top zone 8 to the transfer zone 4.

FIG. 9A shows the same device as in FIG. 8 but with three different sensor elements (e.g. biomass, dissolved oxygen and pH sensors) integrated in the bottom of the bioreactor.

FIGS. 9B and 9C represent the same device shown in perspective. The sensor elements are not represented in FIG. 9C.

Figure 9:
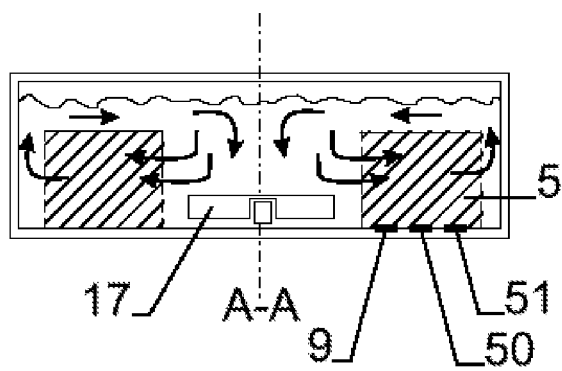
FIG. 9 shows a vertical sectional view (A), a schematic representation of a perspective view of a vertical sectional view (B), and a schematic representation of a perspective view (C) of a cell culture device according to a variant of the third particular embodiment of the first aspect of the present invention.
Figure 9:
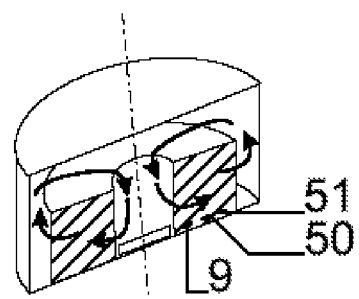
Figure 9:
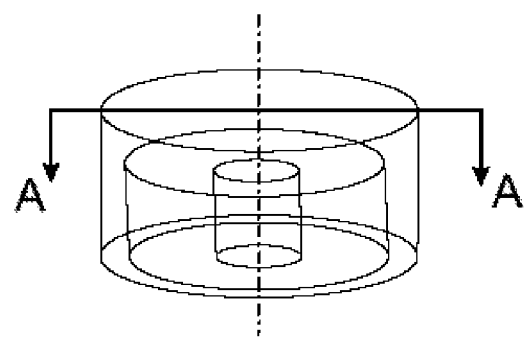

The design of FIG. 7 to 9 has the further advantage that probes (biomass or other kind of probes in addition or instead of the biomass probe) can be implemented directly into the bed with cells. It is relatively easier to construct a cell culture device by integrating the probes on the inner bottom wall of the vessel.

Figure 6:
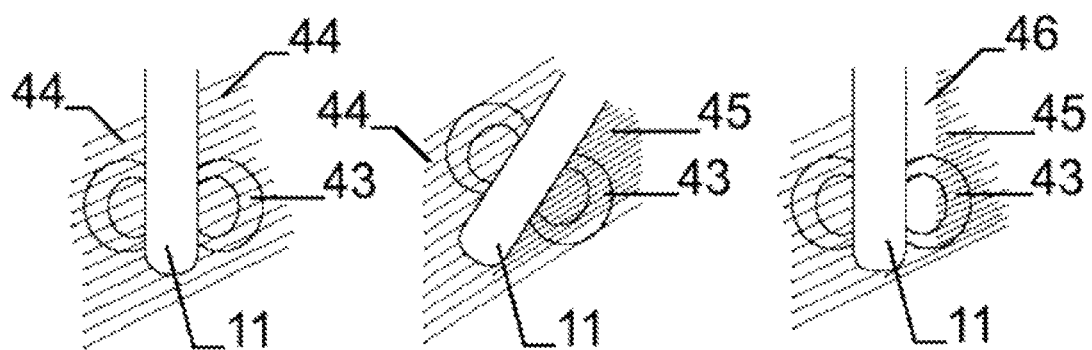
FIG. 6 is a scheme representing a pencil-shaped probe before (left), during (centre), and after a movement (right) in a fixed bed cell culture medium.
Figure 10:
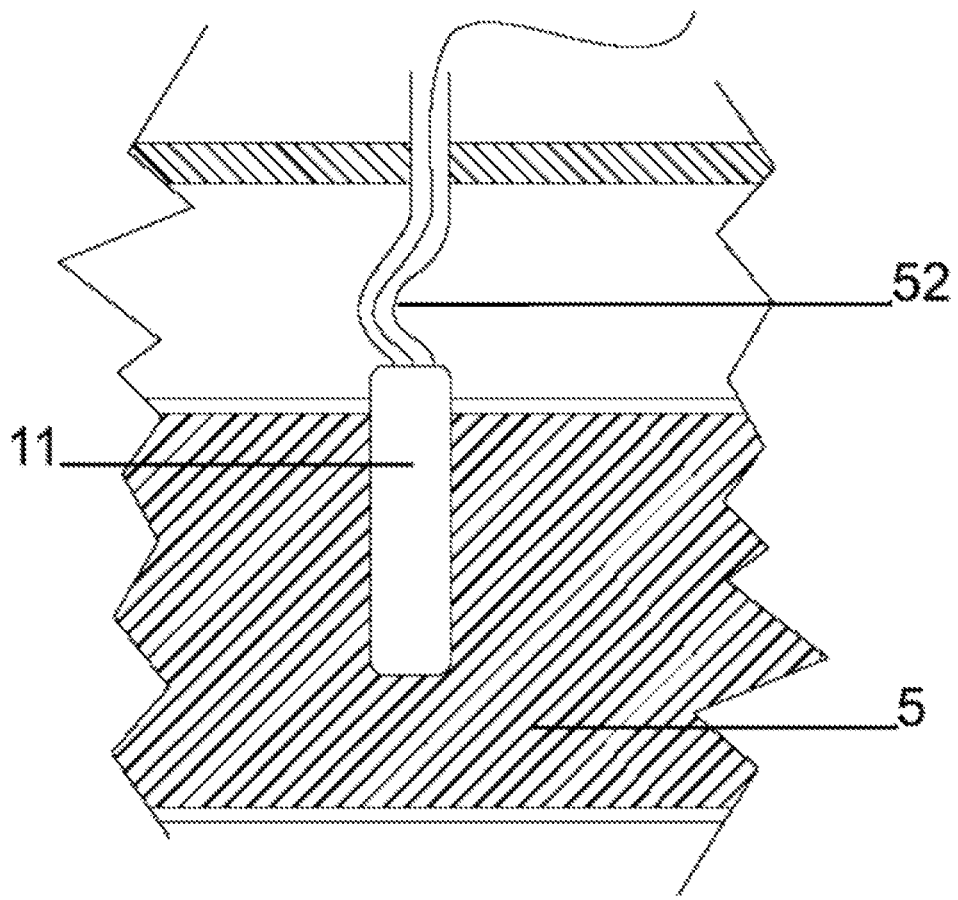
FIG. 10 is a vertical sectional view of part of a cell culture device according to the second particular embodiment of the first aspect of the present invention.

FIG. 10 represents a variant of the second particular embodiment of the first aspect of the present invention. This embodiment represents an alternative to the first particular embodiment to avoid the problem explained in FIG. 6. A sensor element (e.g. a biomass probe) is implemented from the lid, with a flexible part to counterbalance the potential displacement of the lid. The sensor element is solidarized to the fixed bed basket and is connected to measuring equipment via a flexible electrical wire lodged in a flexible tube. In this embodiment, should the lid be displaced by e.g. a gas overpressure (gas overpressure of the order of 10 to 100 mbar are frequently used in bioreactors), the small resulting displacement (typically a few mm) will be absorbed by the flexible tubing containing the electrical wire, without any impact on the probe position. Another illustration of this embodiment can be seen in FIG. 12 where the displacement can be absorbed by the bellows.

Figure 11:
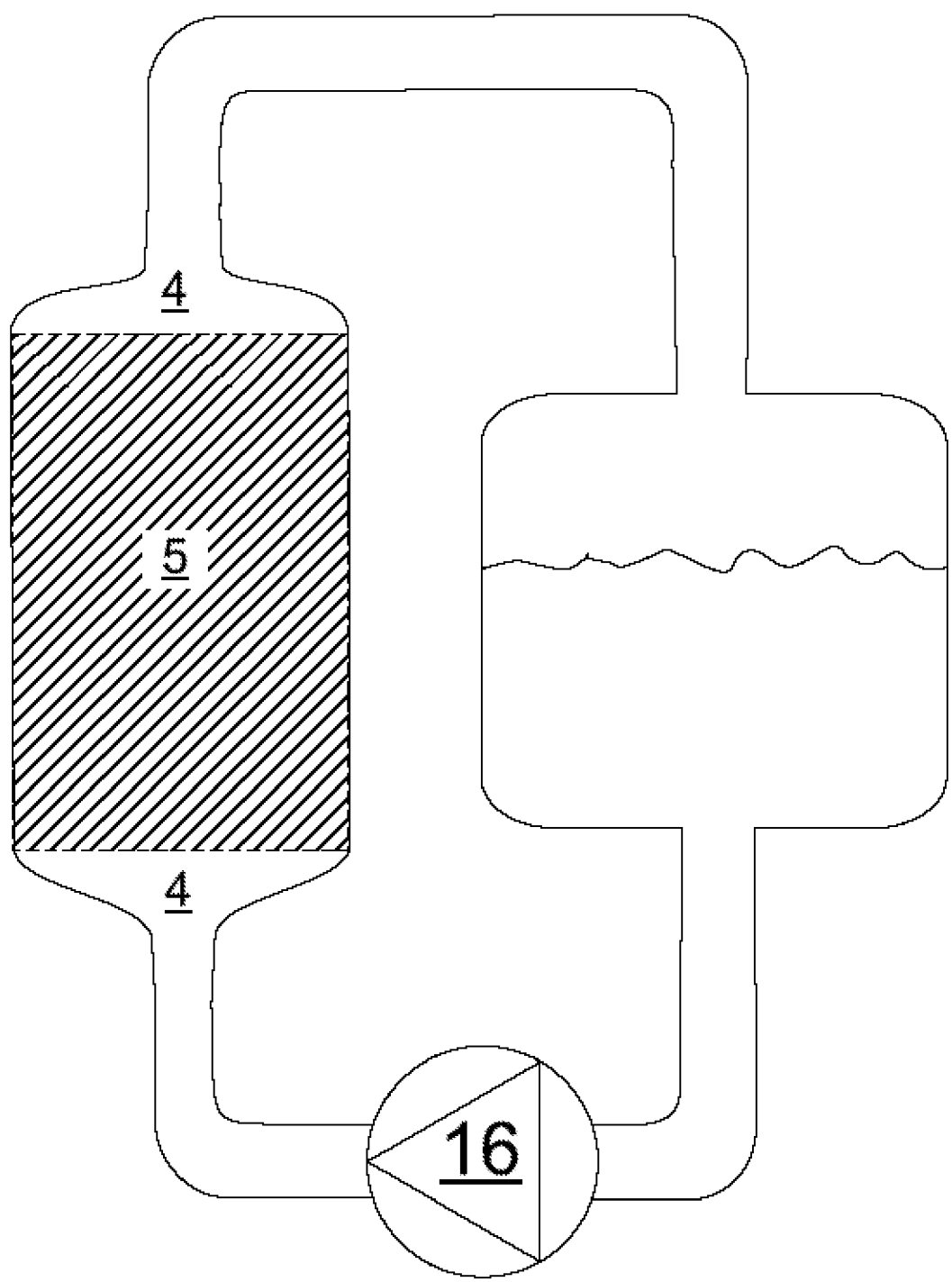
FIG. 11 is a vertical sectional view of a cell culture device according to another embodiment of the first aspect of the present invention.

The concept of the first and the second particular embodiment of the present invention can be generalised to any geometry of fixed bed bioreactors whatever the geometry of the fixed bed, whatever the means for circulating the culture medium. FIG. 11 shows an alternative driving means functioning via an external circulation loop. In FIG. 11, the cell culture device comprises a disposable culture vessel (2) and driving means 16.

Figure 12:
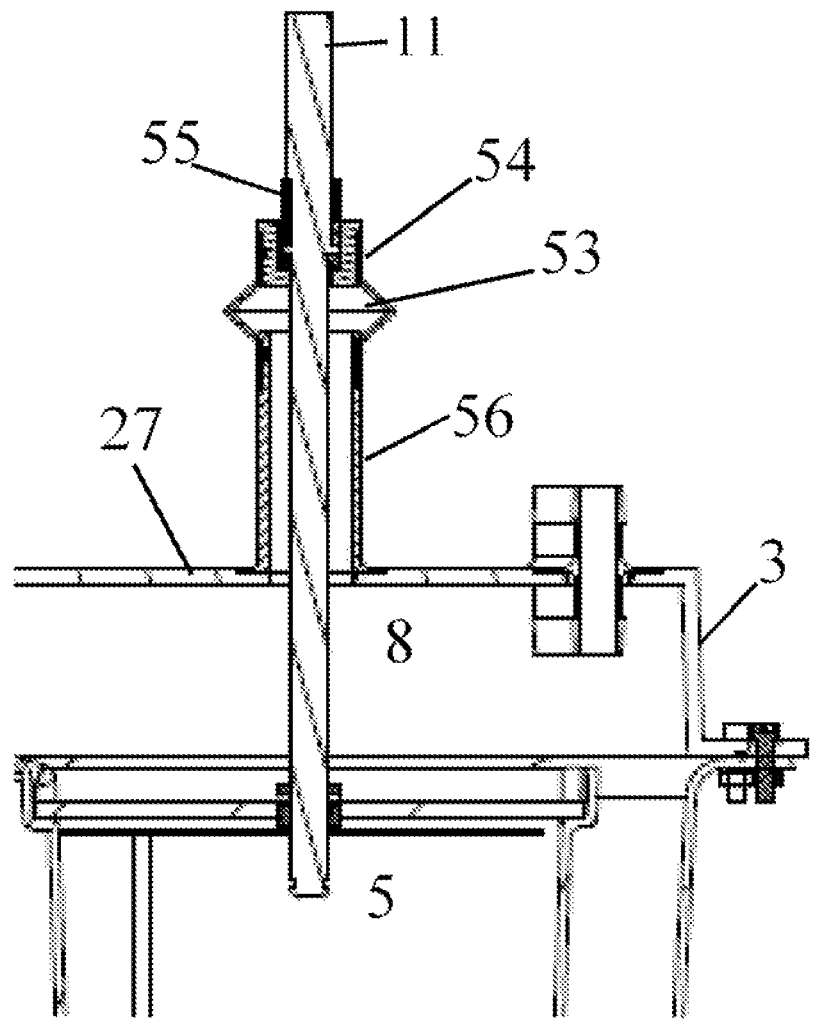
FIG. 12 is a vertical sectional view of part of a cell culture device according to the second particular embodiment of the first aspect of the present invention.

FIG. 12 represents an other variant of the second particular embodiment of the first aspect of the present invention. This embodiment represents an alternative to the first particular embodiment to avoid the problem explained in FIG. 6. A sensor element (e.g. a biomass probe) 11 is implemented in the cell culture zone 5 through a hole in the lid 27. without touching said lid. The sensor element 11 is maintained still in the cell culture zone via a fixation to a tube 56. Tube 56 is mounted on the lid above said hole and comprises a flexible element (bellows 53) to counterbalance the potential displacement of the lid. The tube further comprises a screw thread 54 for attaching the sensor element 11. The sensor element comprises a screw element 55 for fitting in the screw thread 54. The sensor element is solidarized to the fixed bed basket delimiting the cell culture zone 5. In this embodiment, should the lid be displaced by e.g. a gas overpressure (gas overpressure of the order of 10 to 100 mbar are frequently used in bioreactors), the small resulting displacement (typically a few mm) will be absorbed by the bellows, without any impact on the probe position.

While the invention has been illustrated and described in detail in the drawings and foregoing description, such illustration and description are to be considered illustrative or exemplary and not restrictive; the invention is not limited to the disclosed embodiments. Other variations to be disclosed embodiments can be understood and effected by those skilled in the art in practicing the claimed invention, from a study of the drawings, the disclosure, and the appended claims. In the claims, the indefinite article "a" or "an" does not exclude a plurality. The mere fact that certain measures are recited in mutually different dependent claims does not indicate that a combination of these measures cannot be used to advantage. Any reference signs in the claims should not be construed as limiting scope.

The invention claimed is:

1. A cell-culture device comprising: a disposable culture vessel comprising at least one external wall made of a material having a Young modulus E of less than 50 GPa and at least one internal wall, in which there is situated at least one cell culture zone at least partially delimited by the at least one internal wall of the disposable culture vessel, and at least one cell-free medium transfer zone, allowing a flow of a culture medium between the cell culture zone and the transfer zone, and at least one sensor element of a cell-density sensor wherein said sensor element is situated in the cell culture zone of said vessel, wherein the sensor element is an electrode arrangement of at least two measuring electrodes arranged on one of said walls of said cell culture zone and directed towards the cell culture zone.

2. The cell-culture device according to claim 1, wherein said culture vessel is made entirely of a material having a Young modulus E of less than 50 GPa.

3. The cell-culture device according to claim 1, wherein said material is sterilisable and/or electrically insulating.

4. The cell-culture device according to claim 1, wherein said material is a thermoset plastic or a thermoplastic.

5. The cell-culture device according to claim 4, wherein said material is selected from the group consisting of polypropylene, polycarbonate, polyester, polyethylene terephthalate, polyethylene terephthalate glycol and polymethylmethacrylate.

6. The cell culture device according to claim 1, wherein the electrode arrangement is a patch probe or is an electrode arrangement with at least four measuring electrodes integrated into a wall of said cell culture zone, directed toward said cell culture zone.

7. The cell culture device according to claim 1, wherein said at least four measuring electrodes are metal electrodes sputtered and/or plated on a wall of said cell culture zone, directed toward said cell culture zone.

8. The cell culture device according to claim 1, further comprising at least one driving means for driving the flow of the culture medium within the culture vessel and through the cell culture zone of the cell culture device.

9. The cell-culture device according to claim 8, wherein the driving means is situated in the disposable culture vessel.

10. The cell-culture device according to claim 8, wherein said at least one driving means for driving the flow of the culture medium within the culture vessel is situated outside the disposable culture vessel.

11. The cell-culture device according to claim 9, wherein the driving means comprise an impeller suitable for being driven by a drive motor, wherein said impeller is situated in the vessel.

12. The cell-culture device according to claim 11, wherein the drive motor is a magnetic drive and the impeller is a magnetic impeller, wherein said magnetic drive is situated outside the vessel.

13. The cell-culture device according to claim 8, wherein the flow of the culture medium is a circulation through the transfer zone and the cell-culture zone and is driven by the driving means.

14. The cell culture device according to claim 1, wherein said transfer zone is internal to the cell culture zone and in medium communication with said cell culture zone via a top zone and a bottom zone of the vessel, allowing the circulation of the culture medium.

15. The cell-culture device according to claim 14, wherein the impeller is situated in said bottom zone, allowing a circulation of the culture medium from the bottom zone to the top zone through said cell culture zone, and back from the top zone to the bottom zone through said transfer zone.

16. The cell culture device according to claim 1, wherein the culture vessel comprises at least one gas inlet orifice and at least one gas outlet orifice.

17. The cell culture device according to claim 1, further comprising at least one controller device connected to the sensor element for controlling at least one culturing factor depending on the cell density measured by said cell density element.

18. The cell culture device according to claim 1, further comprising a first oxygen or oxygen partial pressure probe located in the at least one cell-free medium transfer zone and a second oxygen or oxygen partial pressure probe in the cell-culture zone.

19. The cell culture device according to claim 1, wherein at least part of said transfer zone is surrounded by said cell culture zone.

20. The cell culture device according to claim 19, wherein said driving means is in said part of said transfer zone which is surrounded by said cell culture zone.

21. A method of culturing cells, using a cell culture device according to claim 1, wherein the cell density of the cell culture is measured by the sensor element.

22. The method according to claim 21, wherein in addition of the measurement of the cell density, at least one culturing factor is determined and/or controlled depending on said measured cell density.

23. The method according to claim 22, further including the step of selecting the culturing factor from the list consisting of the temperature, the flux of the culture medium in the vessel, an introduction rate of a component to be introduced in said cell culture device, a viral infection time, an induction time for a recombinant process, a harvest time and a harvest period.

24. A cell culture device comprising: a disposable culture vessel comprising a casing having at least one external wall made of a material having a Young modulus E of less than 50 GPa and at least one internal wall, in which there is situated at least one cell culture zone at least partially delimited by the at least one internal wall of the disposable culture vessel, and at least one cell free medium transfer zone, allowing a flow of a culture medium between the cell culture zone and the transfer zone, and at least one sensor element at least partly situated in the cell culture zone of said vessel and not in direct contact with the casing of said vessel, wherein said cell culture device further comprises means for decoupling movements of the external or internal walls from movements of the sensor element.

25. A cell culture device according to claim 24, wherein said means for decoupling comprise a flexible element connecting said external wall with said sensor element.

26. A cell culture device according to claim 25, wherein said flexible element is a bellows.

27. A cell culture device according to claim 24, wherein said means for decoupling comprise a non-rigid or wireless transmittal connection for connecting said sensor element to a measuring equipment.

28. A cell culture device comprising:
a culture vessel comprising at least one external wall and at least one internal wall in which there is situated at least one cell culture zone at least partially delimited by the at least one internal wall of the culture vessel, and at least one cell free medium transfer zone, allowing a flow of a culture medium between the cell culture zone and the transfer zone, wherein at least part of said transfer zone is surrounded by said cell culture zone,
at least one driving means for driving the flow of the culture medium within the culture vessel and through the cell culture zone, wherein said driving means is in said part of said transfer zone which is surrounded by said cell culture zone.

29. The cell culture device of claim 28, wherein the driving means is between a first portion of the cell culture zone and a second portion of the cell culture zone.

30. The cell culture device of claim 28, wherein the part of the transfer zone including the driving means is surrounded on at least two lateral sides by the cell culture zone.

31. The cell culture device of claim 1, wherein the sensor element is located on the at least one internal wall of the vessel bounding the cell culture zone.

32. The cell culture device of claim 1, further including an impeller located in the cell-free media transfer zone and surrounded on at least two sides by the cell culture zone.

33. A cell culture device comprising: a culture vessel comprising a casing having at least one external wall made of a material having a Young modulus E of less than 50 GPa, said vessel further including at least one internal wall and a cover, and in which vessel there is situated at least one cell culture zone at least partially delimited by the at least one internal wall of the disposable culture vessel, and at least one cell free medium transfer zone, allowing a flow of a culture medium between the cell culture zone and the transfer zone, and at least one sensor element at least partly situated in the cell culture zone of said vessel and not in direct contact with the casing of said vessel, wherein said cell culture device is configured to decouple movements of at least one wall of the culture vessel from movements of the sensor element.

34. A cell culture device according to claim 24, wherein the sensor element is located at the at least one internal wall delimiting the cell culture zone.

* * * * *